United States Patent [19]

Sosnay

[11] 4,184,259
[45] Jan. 22, 1980

[54] ORTHODONTIC TOOL FOR PLACING TWISTS IN ARCH WIRES

[76] Inventor: Alan J. Sosnay, 55 E. 9th St., New York, N.Y. 10003

[21] Appl. No.: 805,749

[22] Filed: Jun. 13, 1977

[51] Int. Cl.² ............................................. A61C 7/00
[52] U.S. Cl. ....................................... 433/4; 140/149; 140/106; 72/409
[58] Field of Search ................... 32/66; 140/149, 106, 140/118, 121; 81/418, 421, DIG. 5; 72/409, 34, 299

[56] References Cited

U.S. PATENT DOCUMENTS

| | | | |
|---|---|---|---|
| 670,890 | 3/1901 | Burgess | 81/150 |
| 1,523,810 | 1/1925 | Leonard | 32/66 |
| 1,602,119 | 10/1926 | Niebaum | 140/106 |
| 2,396,619 | 3/1946 | Strayer | 81/418 |
| 2,631,617 | 3/1953 | Drayer | 140/117 |
| 3,215,006 | 11/1965 | Urani | 81/3.8 |
| 4,043,364 | 8/1977 | Rose | 32/66 |

*Primary Examiner*—Russell R. Kinsey
*Assistant Examiner*—John J. Wilson
*Attorney, Agent, or Firm*—Frishauf, Holtz, Goodman & Woodward

[57] ABSTRACT

An orthodontic tool for placing and measuring bends or twists in orthodontic arch wires, or the like, in order to place potential torquing forces in the wire, comprises first and second engaging means for engaging an elongated wire on respective opposite surfaces of the wire, one of the engaging means carrying an indicator member with a scale thereon and the other of the engaging means carrying a pointer. When the two engaging means are placed together and twisted around the arch wire, the pointer will indicate the exact degree of twist being placed in the wire on the indicating scale. The engaging means may comprise pliers, keyed members, or the like. Preferably, the scale is interposed between the engaging means to provide a bending space between the engaging means to prevent weakening of the wire when it is twisted. Also disclosed is a tool for bending orthodontic arch wires to provide second order bends.

27 Claims, 13 Drawing Figures

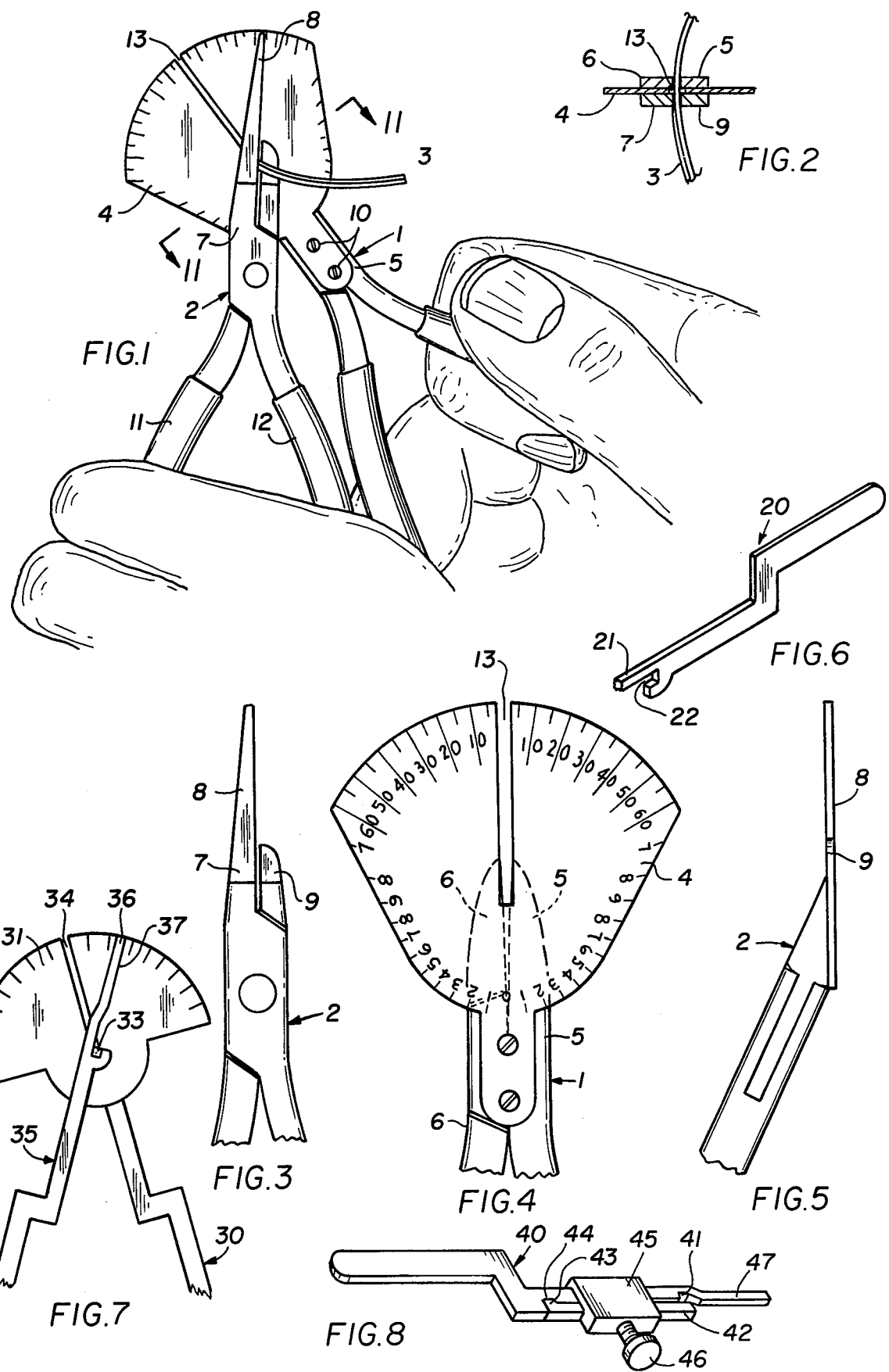

ORTHODONTIC TOOL FOR PLACING TWISTS IN ARCH WIRES

This invention relates to a tool for placing potential torquing forces in an orthodontic arch wire having a generally rectangular or square cross-section, and more particularly to a tool for placing and measuring controlled increments of twist or torsion in such an orthodontic arch wire.

When utilizing the "edgewise" technique of orthodontics, it is very often necessary to bend an orthodontic arch wire at spaced positions along the length thereof in order to apply a torquing force to a tooth. The degree of bend or twist applied to the orthodontic wire will determine the degree of torquing force applied to the tooth. Heretofore, it has been conventional in the art for an orthodontist to use two pairs of pliers gripping a wire at spaced positions along the length thereof, and applying a twist to one pair of pliers relative to the other. The degree of twist was merely estimated by visually observing the wires. Since the wire dimensions are usually less than about 0.0215 by 0.0275 inches, it is impossible to accurately determine the degree of twist placed in the arch wire by visual means. Moreover, a different amount of twist is required for each tooth since the various brackets will be oriented at different angles due to the individual tooth anatomy. Twists in the arch wire are necessary to institute correction forces. Once having put twists on the portions of the arch wire on one side of the mouth, it is usually necessary to duplicate the wire forces on the other side of the mouth. This is very difficult to accomplish at present. No accurate means for determining the degree of twist given to the wires is presently available. Widely varying forces are obtained from one twisted sample of wire to the next using known twisting techniques, thereby providing different degrees of torquing from one tooth to the next and making it difficult to achieve consistent results. A more detailed general discussion of the "edgewise" technique and of the present invention is given below.

The edgewise system of orthodontic treatment employs the use of carefully formed rectangular arch wires which contain within them information in the form of bends and twists to align the teeth into proper occlusion. This is accomplished by first inserting and then ligating this "ideal" rectangular arch into dimensionally close-fitting rectangular slotted edgewise brackets. These brackets are welded to orthodontic bands which girdle the teeth. The net result is a mechanical system of orthodontic treatment which permits precise controlled movements of teeth in every plane of space.

One such movement capable of being produced by the edgewise system is torque. This is accomplished by placing twist at various places along the cross-section of the arch wire. The degree of twist placed in the arch wire and its direction will determine the amount, and the type of torque produced on the tooth crown and roots. The angle that each bracket makes when it rests on the tooth surface will also affect this force system. There are three types of root torque - lingual root torque, lubial root torque and passive root torque, each of which may be required during treatment.

Up to the present, there has been no satisfactory method of producing precise and controlled twist in an arch wire. One reason for this difficulty lies in the tiny cross-sectional dimension of the edgewise arch wire (the largest of which is generally 0.0215×0.0275 inches). The method currently in use today is accomplished by grasping the wire with two pliers which are closely butted up against each other and twisting with one plier while holding steady the other. The degree of twist is then accomplished by visual estimation. The only check available as to the accuracy of the degree of twist actually obtained is to then insert the arch wire into one side of the dental arch and check the degree of vertical displacement that it produces on the other side (before it is inserted in the brackets).

Any corrections will require repeated removal, readjustment and reinsertion of the arch wire. This is a very tedious and time-consuming process. To further complicate matters, it is most often necessary to duplicate the degree of twist on both sides of the arch wire so that symmetrical results may be obtained. This is currently extremely difficult to accomplish if one were just required to place a single uniform degree of twist on each side of the arch wire. It is virtually impossible to accomplish in the current mode if one were to attempt to place more than one degree of twist on each side. This orthodontic requirement is not unusual, since each tooth due to its individual anatomy has its bracket slot oriented at a different angle. In addition, each tooth, depending upon its position in the dental arch, exhibits a different axial inclination and therefore requires a varying amount of torque.

The object of the invention is to provide a tool which will allow for placement of precise amounts of twist about the longitudinal axis of the arch wire. For the first time torquing movements will thus be precisely controlled and no longer left to estimation.

SUMMARY OF THE INVENTION

In the embodiment of the present invention, the above object is achieved by the placement of a protractor-like device on one plier and extending one jaw of the other plier to form a pointer. Thus when the two pliers are placed together after having grasped the arch wire and twisted the plier carrying the pointer will indicate the exact degree of twist being placed in the wire. Keyed wire gripping tools or the like may be used in place of pliers.

The protractor-like device may be designed in a particularly unique manner, employing the use of a "dual" radius. The advantages of this is to permit the operator to adjust the arch wire by holding the pliers or keyed tool in any manner most comfortable to him, and also to exhibit adjustment angles of up to 360°. The larger radius scale is provided to permit greater magnification and hence move precise control of the twist placed in the arch wires. A range of ±60° is generally sufficient because it well exceeds all required degrees of torque required in orthodontics and at the same time limits the protractor size to a dimension permitting ease of manipulation.

In a preferred embodiment, the tool of the present invention utilizes the thickness of the protractor-like device to its advantage. The protractor, being mounted for example on one of the pliers, occupies a position separating the two plier beaks (or key devices) when the wire is being twisted. The thickness of the protractor has been dimensioned to approximately equal that of the thickness of the thickest commonly used wire cross-section. Thus, a space is created between the twisting planes of the arch wires. This space is critical because it prevents weakening of the wire through shear. By incorporating more cross-sectional area between the twisting planes, less molecular strain will occur and a more resilient action results. This translates into a more efficient and precise torquing function on a clinical level.

BRIEF DESCRIPTION OF THE DRAWINGS

FIG. 1 is a side view of an embodiment of the invention in use;

FIG. 2 is a partial sectional view of the embodiment of FIG. 1 along the line II—II in FIG. 1;

FIGS. 3 and 4 are respective side views of the two pairs of pliers of FIG. 1;

FIG. 5 is a side view of the pair of pliers shown in FIG. 3;

FIG. 6 is a perspective view of a modified embodiment of the present invention;

FIG. 7 is a perspective view of another embodiment of the present invention;

FIG. 8 is a perspective view of a modified device of the present invention which is adjustable for different size wires;

DETAILED DESCRIPTION OF THE DRAWINGS

Figure 9:
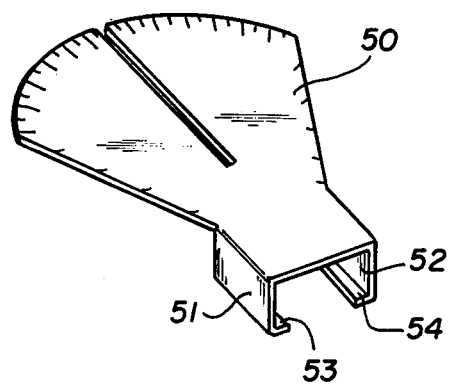
FIG. 9 illustrates a further modification of the present invention using a removable protractor-like scale.

Referring to FIG. 1, two pairs of pliers 1,2 are used to grip an elongated rectangular wire 3, for example an orthodontic arch wire. The pliers 1,2 are shown in greater detail in FIGS. 3-5. The jaws of the respective pliers are designed so as to positively engage side walls of the rectangular arch wire 3 to provide secure, non-slipping engagement. One pair of pliers 1 has a calibrated plate member 4 fixedly attached thereto for example by means of screws 10 (shown), rivets, welding or other suitable means of attachment. Plate member 4 is calibrated in angular subdivisions (see FIG. 4), similar to a protractor, and is hereinafter referred to as a protractor for convenience. The protractor 4 is preferably rigidly connected to one of the jaw members 5 (see FIG. 4) of pliers 1. The other jaw member 6 of pliers 1 is freely movable relative to the protractor 4. One of the jaws 7 of the second pair of pliers 2 has a pointer member 8 extending therefrom which cooperates with the protractor 4 so as to indicate angular bends in the wire 3 about the longitudinal axis of the wire 3. Also, as seen in FIG. 5, the jaws 7,9 of pliers 2 are angulated relative to the handles 11,12 thereof to permit easier manipulation when in the relative positions shown in FIG. 1.

In FIG. 4, the jaws 5, 6 of pliers 1 are shown slightly opened.

The protractor 4 has an elongated slot 13 therein which is larger than the largest dimension of a wire which the tool of the present invention is to be used to twist. In use, the two pliers are manipulated to grip the wire 3 with the protractor 4 interposed between the jaws thereof, as indicated in FIG. 2. The thickness of the protractor 4 provides a twisting space between the jaws of the two pairs of pliers so that the wire may be twisted without unduly working the metal of the wire. This prevents weakening of the wire through shear when it is being twisted. The larger the spacing between the two pairs of pliers (i.e., the greater the thickness of protractor 4), the less molecular strain will occur in the wire and a more resilient action results during use of the twisted wire. This means that the wire will produce a more efficient and precise torquing function on a clinical level. It has been found satisfactory to make the thickness of protractor 4 about equal to the thickness of the wires to be twisted.

The protractor 4 may be provided in any desired shape. For example, round is a visually pleasing shape and does not exhibit any outstanding sharp edges. However, the dual radius protractor shown in FIG. 4 is particularly advantageous since the larger radius portion, for example from ±60°, provides a greater magnification of the index lines, thereby permitting more precise control of the twist placed in the arch wire. For the remaining angles through 360°, the radius of the protractor 4 relative to the center thereof (that is, the end point of the slot 13) is reduced in order to reduce the bulk of the instrument, to make it easier to manipulate the instrument and to improve the visual appearance thereof.

FIG. 6 illustrates a key member 20 which may either replace the pliers 2 or which may have a protractor secured thereto (as shown in FIG. 7). In the event that the key member 20 replaces the pliers 2, the key member is provided with a pointer 21 which extends from the body thereof and which serves the same purpose of the pointer 8 of pliers 2. The key member 20 has a key slot 22 formed therein for non-rotationally gripping a rectangular or a square cross-section arch wire. The operation of the key member 20 is self-explanatory. The pointer 21 may be integrally formed with the main body portion of the key member 20 or may be attached thereto.

FIG. 7 illustrates a key member 30 having a protractor 31 formed in one solid piece with the key member 30 or attached thereto, the portion of the key 30 behind the protractor 31 having a key slot, such as the key slot 22 of FIG. 6, for non-rotationally engaging an arch wire 33. The protractor 31 has a slot 34 therein through which the arch wire may pass. The slot 34 is wide enough to permit complete twisting of the arch wire therein. A second key member 35 is provided which has a pointer 36 thereon, the key member 35 serving the function of pliers 2 in FIG. 1. The pointer 36 may be narrower than as shown in FIG. 7, or, for example, it may be calibrated such that the leading edge 37 thereof serves as the indicator edge. With the embodiment of FIG. 7, best results are obtained when a different set of key members 30, 35 are used for each different size wire to be twisted. This is necessary in order to obtain highly accurate twisting results.

When the key member of FIG. 6 is used in place of the pliers 2 and in conjunction with the pliers 1 with a protractor mounted thereon, it is only necessary to provide different key members 20 for different size wires. The pliers 1 with the protractor 4 mounted thereon can be used for any size wire.

FIG. 8 illustrates an adjustable key member 40 which can be used in place of the key member 20 of FIG. 6 or the key member 35 of FIG. 7. The adjustable key member 40 of FIG. 8 may also be used in place of the key member 30 with a protractor mounted thereon, if desired. The key member 40 has a partial notch 41 formed therein and an adjustable leg member 42 which defines another wall of the notch 41. The leg member 42 has a projection 43 which fits within a mating depression 44 in the main portion of the key member 40. Further provided is a generally C-shaped clamp 45 with an adjusting screw 46 thereon. The clamp 45 retains the movable leg 42 relative to the main body of the key member 40. The key member 40 further includes a pointer member 47 at the end thereof for cooperating with a protractor. In use, a wire is inserted in the slot 41 and the adjusting screw 46 is tightened so as to firmly clamp the movable leg 42 against the wire to retain the wire in the notch 41. This adjustment mechanism enables the key member 40 to be useful for a variety of different sized rectangular or square arch wires. Other adjusting mechanisms, of course, could be provided.

FIG. 9 illustrates a protractor 50 which is removable from a pair of pliers or from a key member, for example a key member shown in FIGS. 6 or 7. The protractor 50 includes at the end thereof resilient leg members 51, 52 having in-turned ends 53, 54, respectively. In use, the spacing between the legs 51, 52 is sufficient to enable the legs 51, 52 to snap over the pivot box portion of, for example, a pair of pliers, or to snap over a key member. Preferably, the leg members 51, 52 are of a relatively springy material so that they may be easily placed on the pliers and yet be firmly retained thereon. The legs 51,52 may be shortened so that turned-in ends 53,54 abut against the side walls of the pivot box portion of the pliers, the plier side walls being grooved or the like to receive the ends 53,54 in the grooves. This positively and accurately locates the protractor 50 on the pliers. Similar provisions could be provided for the key members of FIGS. 6–8 to provide a removable protractor therefor. If desired, a clamp such as clamp 45 of FIG. 8 can be used to clamp the removable protractor of FIG. 9 to a pair of pliers or to a key member.

Figure 10:
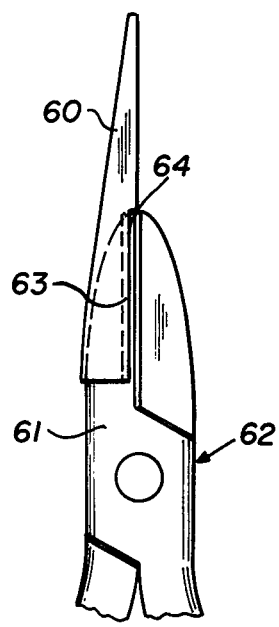
FIG. 10 illustrates pliers with a removable pointer in accordance with the present invention.

FIG. 10 illustrates a pair of pliers 62 with a removable pointer 60. The pointer 60 is attached to jaw 61 by means of portions 63 on both sides of jaw 61 springingly engaging grooves 64 on both sides of jaw 61. The portion 63 is shown only on one side of jaw 61. The rear of jaw 61 is similarly constructed to receive a respective portion 63.

Figure 11:
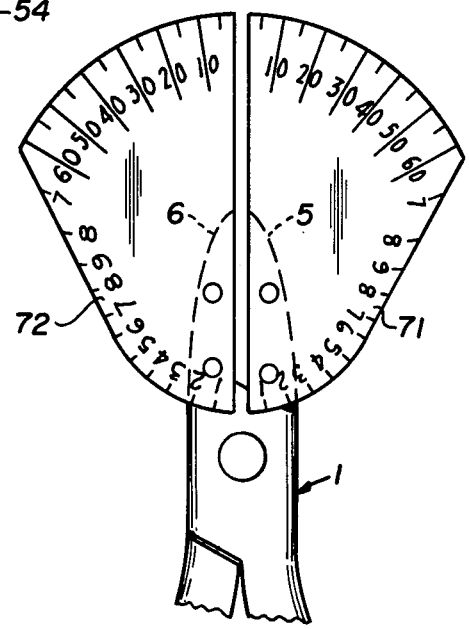
FIG. 11 illustrates a modification to the embodiment of FIG. 4.

FIG. 11 shows an embodiment with a split protractor comprised of portions 71 and 72 which are respectively attached to jaws 5,6 of pliers 1. The protractor portions may be removably attached to respective jaws 5,6 in a similar manner as protractors 50 of FIG. 9 is attached, except that the springy attachment portions would, for example, engage the sides of the respective jaws 5,6.

Figure 12:
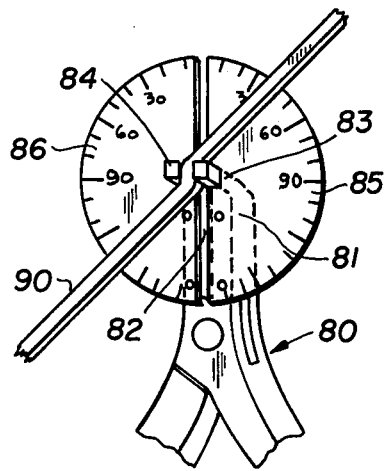
FIGS. 12 and 13 illustrate another modification of the present invention.
Figure 13:
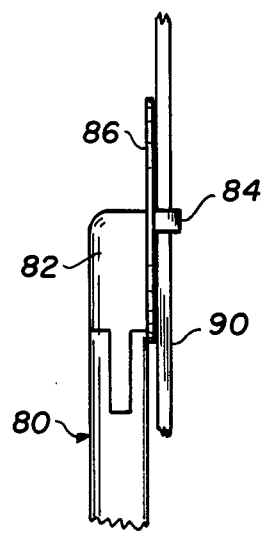

FIGS. 12 and 13 illustrate respective side and top views of a further embodiment of the invention which is particularly useful in placing bends in orthodontic arch wires 90, or the like. Such bends, as illustrated in FIG. 12, are generally termed "second order bends" in the orthodontic art. As shown in FIGS. 12 and 13, a plier 80 has respective jaws 81,82 with bent over (i.e., angulated) tip portions 83,84, respectively. The tip portions of the jaws of the pliers are adapted to engage an orthodontic arch wire. The jaws 81,82 respectively carry segments of an indicating protractor 85,86, the protractor segments 85,86 being attached to the respective jaws by means of riveting, screws, welds, adhesives, or any other suitable method. The tip portions of the jaws of the pliers, which engage the arch wire, are preferably located centrally of the protractor formed by segments 85,86 so that the device can indicate bends through 360° and can indicate and measure bends on both sides of the plier jaws, such as seen in FIG. 12.

The angulated tip portions 83,84 of the pliers extend outwardly past the front surface of the protractor segments as can be readily seen in FIG. 13. These extending portions of the bent over tips of the pliers define a bending point for the wire. The arch wire, or the like, may be bent by hand or by using another tool, such as another pair of pliers, to grip the wire adjacent the bending point defined by the tips of pliers 80. The angle of bending is clearly indicated on the scale on the protractor segments 85,86. Very precise bends can be obtained with the apparatus illustrated in FIGS. 12 and 13.

The apparatus of FIGS. 12 and 13 may be modified by using pliers with straight jaws and by mounting the protractor near or at the tips of the jaws with the flat face of the protractor oriented substantially perpendicularly to the jaws. While this embodiment would be operable, it is less convenient since the protractor segments will be more prone to damage and the tool will require more space for storage. Alternatively, the pliers 80 may be replaced by a key having a fixed or adjustable opening for gripping a wire and defining the bending point. For example, the keys of FIG. 6 or 8 may be modified by bending the wire engaging portions at a right angle to the body of the key and by securing a protractor similarly as shown in FIGS. 12 and 13. Alternatively, the protractor may be mounted perpendicular to the longitudinal axis of the keys shown in FIGS. 6 and 8, without bending over the wire engaging portions of the keys. The key and protractor can be made integral with each other.

The protractor of FIGS. 12 and 13 can be made in one piece, secured to one jaw or the pivot box, and have a slot or opening in the central portion thereof to permit relative movement of the jaws to engage and disengage arch wires or the like.

While the invention has been described above with respect to specific embodiments, it should be clear that various modifications and alterations could be made thereto within the scope of the invention as defined in the appended claims.

I claim:

1. An orthodontic tool for placing and measuring twists in an arch wire, or the like, the arch wire having a longitudinal axis and at least two opposing substantially flat side surface portions extending along said longitudinal axis, said twists being made about said longitudinal axis, within the boundaries of said opposing substantially flat side surface portions, the tool comprising:

first engaging means for engaging opposing substantially flat side surface portions of said arch wire or the like, and being substantially non-rotatable relative to said side surface portions engaged thereby;

second engaging means for engaging opposing substantially flat side surface portions of said arch wire or the like, and being substantially non-rotatable relative to said side surface portions engaged thereby;

said first and second engaging means extending substantially parallel to each other and both extending substantially perpendicularly to said longitudinal axis of said engaged arch wire and to the extending direction of said respective opposing substantially flat side surface portions of said arch wire or the like which are engaged thereby, and said first and second engaging means being movable relative to each other to twist said arch wire or the like about its longitudinal axis substantially without bending the longitudinal axis of the arch wire or the like;

indicating means on one of said engaging means and having an angle indicating scale thereon, said indicating means extending substantially parallel to said one engaging means and substantially perpendicularly to said longitudinal axis of said engaged arch wire or the like; and pointer means on the other of said engaging means, said pointer means extending substantially parallel to said other engaging means and substantially parallel to said angle indicating scale on said indicating means when both of said engaging means are in said engagement with said arch wire or the like, said pointer means cooperating with said angle indicating scale to indicate the degree of twisting of said arch wire or the like, about said longitudinal axis of said arch wire or the like when said engaging means are turned relative to each other about said longitudinal axis while in engagement with said arch wire or the like.

2. An orthodontic tool according to claim 1 wherein said indicating means is interposed between said first and second engaging means to provide a twisting space therebetween.

3. An orthodontic tool according to claim 1 wherein said indicating means is a plate-like protractor-like device having a slot therein for permitting said arch wire, or the like, to pass therethrough.

4. An orthodontic tool according to claim 3 wherein said indicating means is at least a segment of a circle.

5. An orthodontic tool according to claim 3 wherein said indicating means is comprised of two portions, each of which have different radii of curvature, each portion having a scale thereon.

6. An orthodontic tool according to claim 1 wherein at least one of said first and second engaging means comprises a pair of pliers.

7. An orthodontic tool according to claim 6 wherein said engaging means which carries said indicating means comprises a pair of pliers.

8. An orthodontic tool according to claim 7 wherein said other of said first and second engaging means comprises a pair of pliers having two jaws, one of said jaws having an elongated portion which comprises said pointer.

9. An orthodontic tool according to claim 7 wherein said pair of pliers carrying said indicating means comprises two cooperating separated segments which are coupled to respective ones of said jaws.

10. An orthodontic tool according to claim 1 wherein said other of said first and second engaging means comprises a pair of pliers having two jaws, one of said jaws having an elongated portion which comprises said pointer.

11. An orthodontic tool according to claim 1 wherein said second engaging means is spaced from said first engaging means along the longitudinal axis of said elongated arch wire, or the like.

12. An orthodontic tool according to claim 1 wherein at least one of said engaging means comprises a key-member having a handle and a slot therein for engaging opposing side surfaces of an arch wire, or the like.

13. An orthodontic tool according to claim 12 wherein said pointer means comprises an elongated member extending from said key-member for cooperating with said indicating means.

14. An orthodontic tool according to claim 12 wherein both of said engaging means comprises a key-member, each having a handle and a respective slot therein for engaging said opposing side surfaces of an arch wire, or the like.

15. An orthodontic tool according to claim 14 wherein one of said key-members has said indicating means thereon, and the other of said key-members has said pointer means thereon.

16. An orthodontic tool according to claim 12 wherein said key member has said indicating means mounted thereon.

17. An orthodontic tool according to claim 12 wherein said key member includes means for adjusting the width of the slot therein so as to accommodate arch wires, or the like, of different cross-sectional dimensions.

18. An orthodontic tool according to claim 17 wherein slot adjusting means comprises a movable member defining at least one wall of said slot, and means for clamping said movable member against an arch wire received in said slot.

19. An orthodontic tool according to claim 1 wherein said indicating means is removably mounted on said one of said engaging means.

20. An orthodontic tool according to claim 1 wherein said pointer means is removably mounted on said other of said engaging means.

21. An orthodontic tool according to claim 1 wherein said indicating means is non-movable relative to said one of said engaging means when in use.

22. An orthodontic tool according to claim 1 wherein said pointer means is non-movable relative to said other of said engaging means when in use.

23. An orthodontic tool according to claim 1 wherein said indicating means is a plate-like member coupled to said one of said engaging means.

24. An orthodontic tool for placing and measuring bends or twists in an arch wire, or the like, the arch wire having a longitudinal axis and at least two opposing substantially flat side surface portions extending along said longitudinal axis, said bends or twists being made about said longitudinal axis and within the boundaries of said opposing substantially flat side surface portions, the tool comprising:

a first pair of pliers having two jaws for respectively engaging opposing substantially flat side surface portions of said arch wire or the like, and being substantially non-rotatable relative to said side surface portions engaged thereby;

a second pair of pliers having two jaws for respectively engaging opposing substantially flat side surface portions of said arch wire or the like, and being substantially non-rotatable relative to said side surface portions engaged thereby; and indicating means on said first pair of pliers and having an angle indicating scale thereon;

one of the jaws of said second pair of pliers having an elongated portion which comprises a pointer means, said pointer means extending substantially parallel to said angle indicating scale on said indicating means and cooperating with said angle indicating scale to indicate the degree of bending or twisting of said arch wire or the like about said longitudinal axis of said arch wire or the like.

25. An orthodontic tool according to claim 24 wherein said indicating means is interposed between said first and second pairs of pliers to provide a bending or twisting space therebetween.

26. An orthodontic tool according to claim 25 wherein said indicating means is a plate-like protractor-like device attached to said first pair of pliers.

27. An orthodontic tool according to claim 24 wherein said first and second pairs of pliers are spaced from each other along the longitudinal axis of said elongated arch wire or the like to provide a bending or twisting space therebetween.

* * * * *